US007826763B2

(12) United States Patent
Doshohda et al.

(10) Patent No.: US 7,826,763 B2
(45) Date of Patent: Nov. 2, 2010

(54) OZONE REMOVAL DEVICE, IMAGE FORMING APPARATUS HAVING THE SAME, AND METHOD FOR REMOVING OZONE

(75) Inventors: Hiroshi Doshohda, Chiba (JP); Katsumi Adachi, Nara (JP); Toshiaki Kagawa, Nara (JP)

(73) Assignee: Sharp Kabushiki Kaisha, Osaka (JP)

( * ) Notice: Subject to any disclaimer, the term of this patent is extended or adjusted under 35 U.S.C. 154(b) by 67 days.

(21) Appl. No.: 12/042,511

(22) Filed: Mar. 5, 2008

(65) Prior Publication Data

US 2008/0219695 A1 Sep. 11, 2008

(30) Foreign Application Priority Data

Mar. 7, 2007 (JP) ............................. 2007-057869
Oct. 31, 2007 (JP) ............................. 2007-284536

(51) Int. Cl.
*G03G 21/20* (2006.01)
*G03G 15/08* (2006.01)
*G03G 15/02* (2006.01)
*A61L 9/00* (2006.01)

(52) U.S. Cl. ........................... 399/93; 399/58; 399/173; 422/29

(58) Field of Classification Search ................... 399/93, 399/173; 250/423 R
See application file for complete search history.

(56) References Cited

U.S. PATENT DOCUMENTS 3,977,848 A * 8/1976 Oliphant ........................ 96/19
4,040,731 A * 8/1977 Nishikawa ................... 399/93
4,401,385 A * 8/1983 Katayama et al. ............. 399/93
5,445,798 A * 8/1995 Ikeda et al. ................. 422/121
5,521,383 A * 5/1996 Furukawa et al. ........... 250/324
5,742,874 A * 4/1998 Koshimura et al. ......... 399/100
6,103,190 A * 8/2000 Tanimura et al. .............. 422/29

(Continued)

FOREIGN PATENT DOCUMENTS

JP 02-042462 2/1990

(Continued)

OTHER PUBLICATIONS

Kagawa et al., Electronic Apparatus, Specification, Claims, Abstract, and Drawings for co-pending U.S. Appl. No. 12/042,134 filed Mar. 4, 2008, 112 pages.

(Continued)

*Primary Examiner*—David M Gray
*Assistant Examiner*—Francis Gray
(74) *Attorney, Agent, or Firm*—Renner, Otto, Boisselle & Sklar, LLP

(57) ABSTRACT

A color laser printer is provided with a first exhaust duct for exhausting ozone generated by a charging unit etc. inside a housing to the outside of the housing. The first exhaust duct is therein provided with a catalytic honeycomb filter for ozone gas treatment and an ion emitting unit for emitting negative ions into an atmosphere. Most of an ozone gas component is decomposed and/or absorbed by the catalytic honeycomb filter for ozone gas treatment. Furthermore, the residual ozone gas component is decomposed by the negative ions generated by the ion emitting unit. This arrangement makes it possible to provide a new ozone removal device which is different from an ozone decomposing filter or a heat source.

16 Claims, 7 Drawing Sheets

U.S. PATENT DOCUMENTS

| | | | | |
|---|---|---|---|---|
| 6,235,090 | B1 * | 5/2001 | Bernstein et al. | 96/57 |
| 6,373,680 | B1 * | 4/2002 | Riskin | 361/231 |
| 6,577,828 | B1 * | 6/2003 | Ramos | 399/93 |
| 7,199,993 | B2 * | 4/2007 | Kato et al. | 361/231 |
| 2003/0072675 | A1 | 4/2003 | Takeda et al. | |
| 2005/0077103 | A1 * | 4/2005 | Ikeda et al. | 181/225 |
| 2005/0238381 | A1 | 10/2005 | Song et al. | |
| 2005/0271414 | A1 * | 12/2005 | Katayama et al. | 399/93 |
| 2006/0268490 | A1 * | 11/2006 | Joannou et al. | 361/220 |
| 2007/0212111 | A1 * | 9/2007 | Kagawa et al. | 399/168 |
| 2008/0130190 | A1 * | 6/2008 | Shimada | 361/231 |
| 2008/0217556 | A1 * | 9/2008 | Kagawa et al. | 250/423 R |

FOREIGN PATENT DOCUMENTS

| | | |
|---|---|---|
| JP | 2002-095731 | 4/2002 |
| JP | 2002-268483 | 9/2002 |
| JP | 2004-164918 | 6/2004 |
| JP | 2004-319183 | 11/2004 |
| JP | 2005-004144 | 1/2005 |
| JP | 2005-055515 | 3/2005 |
| JP | 2005-056607 | 3/2005 |
| JP | 2005-065838 | 3/2005 |
| JP | 2005-149901 | 6/2005 |
| JP | 2005-316366 | 11/2005 |
| JP | 2006-39168 | 2/2006 |
| JP | 2007-47496 | 2/2007 |
| JP | 2008-052065 | 3/2008 |
| KR | 2001100367 A * | 11/2001 |

OTHER PUBLICATIONS

Kagawa et al., Electronic Apparatus, Filing Receipt for co-pending U.S. Appl. No. 12/042,134 filed Mar. 4, 2008, 3 pages.

* cited by examiner

OZONE REMOVAL DEVICE, IMAGE FORMING APPARATUS HAVING THE SAME, AND METHOD FOR REMOVING OZONE

This Nonprovisional application claims priority under 35 U.S.C. §119(a) on Patent Application No. 057869/2007 filed in Japan on Mar. 7, 2007 and Patent Application No. 284536/2007 filed in Japan on Oct. 31, 2007, the entire tents of which are hereby incorporated by reference.

FIELD OF THE INVENTION

This invention relates to an ozone removal device for removing ozone in an atmosphere, a method for removing ozone, and an image forming apparatus including the ozone removal device.

BACKGROUND OF THE INVENTION

A process for charging an image carrier such as a photosensitive drum and a process for transferring a toner image on the image carrier to a recording paper or an intermediate transfer belt are absolutely required for an image forming apparatus based on the electrophotographic process. A charger and a transferor of a contact-type which are roller-shaped or brush-shaped can be employed for the processes. Due to contact with the image carrier and the intermediate transfer belt, the charger and the transferor suffer from friction damage. For that reason, recently, the charger, the transferor, etc. of a contact-type have been employed only for a relatively slow electrophotographic process. A high-speed electrophotographic process employs a corona charger (of a scorotron charger method etc.) Although the corona charger is suitable for the high-speed electrophotographic process, ozone generation is inevitable due to the structure thereof. Due to generation of ozone with a high concentration inside an image forming apparatus by the corona charger, products of ozone (such as NOx) adhere to the surface of the photoreceptor. This would cause a charge diffusion of the photoreceptor and result in an image defect, what is called an image blurring.

In order to prevent this, a general image forming apparatus is provided with an exhaust duct for forcibly exhausting ozone in the apparatus outside with an exhaust fan. Another type of an image forming apparatus is arranged such that a concentration of ozone to be exhausted outside the apparatus is reduced by further provision of an ozone decomposing filter inside the exhaust duct for exhausting ozone.

The ozone decomposing filter is applied not only to the image forming apparatus based on the electrophotographic process but also to an electrostatic air cleaning apparatus for dust, a waste ozone treatment device for an oxidation apparatus based on oxidizability of ozone, a preservation apparatus for fruits and vegetables utilizing an antiseptic effect of ozone, etc.

In addition to the ozone decomposing filter, Japanese Unexamined Patent Publication No. 42462/1990 (Tokukaihei 2-42462 (published on Feb. 13, 1990)) discloses a technique for heat decomposition of ozone with a heat source provided inside an exhaust duct for exhausting ozone.

SUMMARY OF THE INVENTION

However, the conventional ozone removal techniques have the problems below.

In the case of the ozone decomposing filter, an ability of the filter to decompose ozone decreases with time. Accordingly, this entails an expenditure of required periodic replacement of the filter. Besides, the replacement of the filter is troublesome because a user needs to dismount a device or call a serviceperson.

In the case of the heat source, a temperature thereof needs to be raised to at least 100° C. or more. For example, the temperature of the heat source needs to be raised between 120° C. and 150° C. in order to decompose approximately 50% of ozone while one transfer paper is printed out. A cost burden of electricity consumption is heavy because such a temperature raise requires a large amount of electricity.

The present invention was made in view of the aforementioned problems. An object of the present invention is to provide a new type of an ozone removal device which is different from the ozone decomposing filter, the heat source, or the like.

In order to attain the object, the ozone removal device of the present invention includes an ion emitting section for emitting negative ions into an atmosphere containing ozone.

As a result of a keen examination on a method for removing ozone, the inventors of the present invention found that the negative ions emitted into an atmosphere have an ozone reduction effect although the mechanism of this action is unclear. According to the arrangement, the ion emitting section emits the negative ions into an atmosphere and thereby an ozone concentration is reduced. Thus, ozone removal can be carried out.

According to the arrangement, there is no need to use an ozone decomposing filter for ozone removal. Therefore, this arrangement makes it possible to save user's trouble because the replacement of the filter is not required. This arrangement also makes it possible to hold electricity consumption down because a large amount of electricity is not required for heat decomposition.

Additional objects, features, and strengths of the present invention will be made clear by the description below. Further, the advantages of the present invention will be evident from the following explanation in reference to the drawings.

DESCRIPTION OF THE EMBODIMENTS

Embodiment 1

An embodiment of the present invention is described below with reference to FIGS. 1 to 5. The present embodiment describes a case where the ozone removal device of the present invention is applied to a color laser printer, which is an image forming apparatus.

Figure 2:
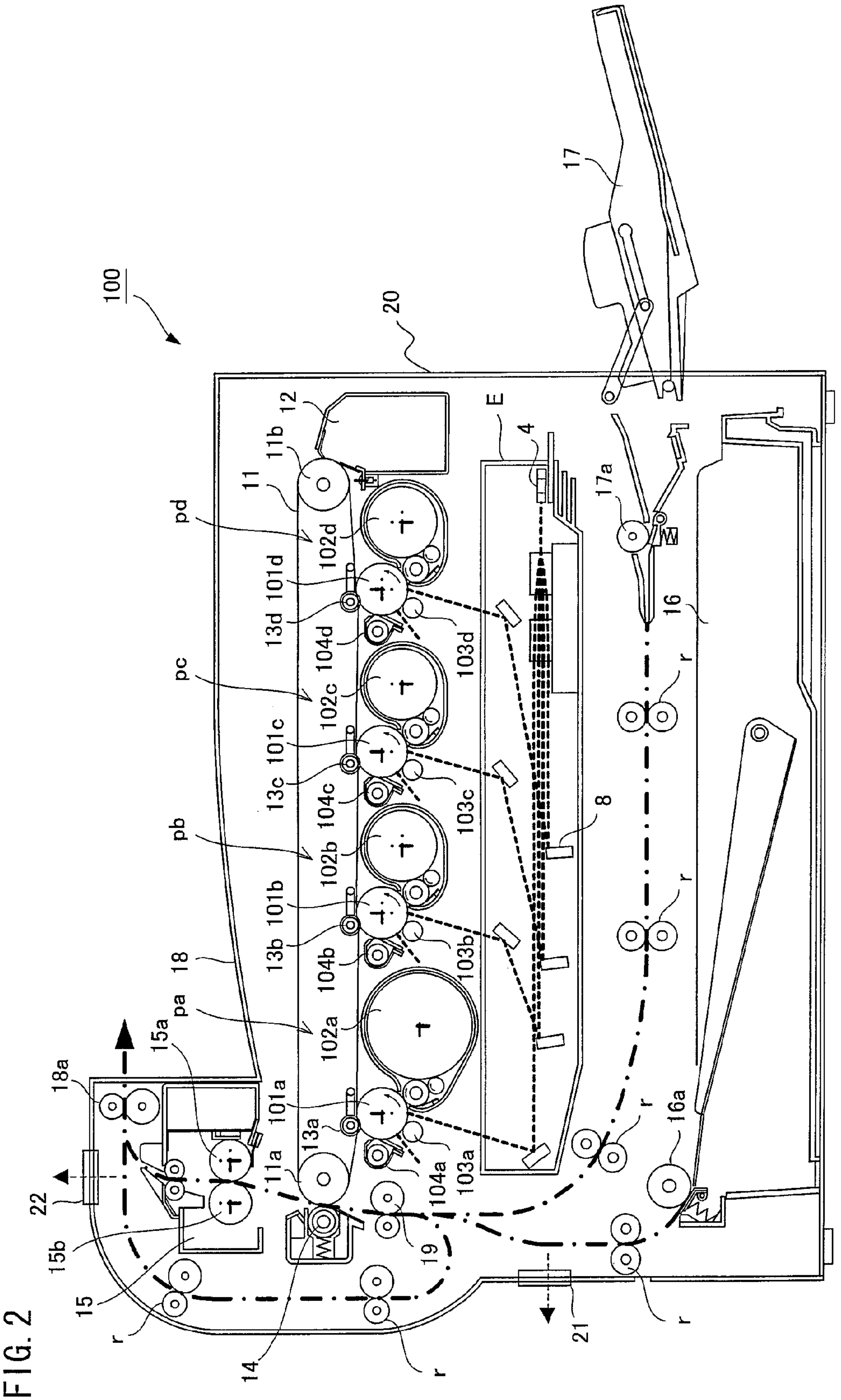
FIG. 2 is a cross-sectional view illustrating a schematic structure of the color laser printer in accordance with the embodiment of the present invention.

FIG. 2 is a longitudinal sectional view illustrating a schematic structure of a color laser printer (image forming apparatus) 100 in accordance with one embodiment of the present invention. As illustrated in FIG. 2, the color laser printer 100 of the present embodiment includes an optical system unit E, four visible image forming units pa, pb, pc, and pd, an intermediate transfer belt 11, a secondary transferring unit 14, a fixing unit 15, an internal paper feeding unit 16, a manual paper feeding unit 17, and a housing 20 containing these members.

The visible image forming unit pa includes a photoreceptor 101*a*, a charging unit 103*a*, a developing unit 102*a*, a cleaning unit 104*a*, and a primary transferring unit 13*a*. The photoreceptor 101*a* is a carrier of a toner image. The charging unit 103*a*, the developing unit 102*a*, and the cleaning unit 104*a* are provided around the photoreceptor 101*a*. The primary transferring unit 13*a* is provided in such a manner that the primary transferring unit 13*a* is pressed against the photoreceptor 101*a* with the intermediate transfer belt 11 therebetween. Other three visible image forming units pb, pc, and pd are configured in the same manner as the visible image forming unit pa. The developing units of the visible image forming units contain color toners of yellow (Y), magenta (M), cyan (C), and black (K), respectively.

The optical system unit E includes a light source 4, a plurality of mirrors, etc. Light from the light source 4 is irradiated to each of photoreceptors 101*a*, 101*b*, 101*c*, and 101*d* by the optical system unit E. The intermediate transfer belt 11 is stretched by tension rollers 11*a* and 11*b* without sag. A waste toner box 12 is provided in contact with the intermediate transfer belt 11 so as to be on the side of the tension roller 11*b*. The secondary transferring unit 14 is provided in contact with the intermediate transfer belt 11 so as to be on the side of the tension roller 11*a*.

The fixing unit 15 is provided downstream of the secondary transferring unit 14. The fixing unit 15 includes a heating roller 15*a* and a pressure roller 15*b*. The heating roller 15*a* and the pressure roller 15*b* are pressed against each other at a predetermined pressure by force means which is not shown in FIG. 2.

Image forming processes of the color laser printer 100 are described below. Firstly, the surface of the photoreceptor 101*a* is uniformly charged by the charging unit 103*a*. The optical system unit E performs laser exposure on the charged surface of the photoreceptor 101*a* in accordance with image information, thereby forming an electrostatic latent image. Secondly, the developing unit 102*a* develops a toner image from the electrostatic latent image on the photoreceptor 101*a* with the toner. The developed toner image is transferred on the intermediate transfer belt 11 by the primary transferring unit 13*a* to which a bias voltage electrically opposite to that of the toner is applied. As a result, a black toner image is transferred on the intermediate transfer belt 11. Similarly, toner images of yellow, cyan, and magenta are transferred on the intermediate transfer belt 11 by the other visible image forming units pb, pc, and pd.

The toner image on the intermediate transfer belt 11 is conveyed to the secondary transferring unit 14. By applying a bias voltage electrically opposite to that of the toner to the secondary transferring unit 14, the toner image is transferred onto a recording paper which is fed by a paper feeding roller 16a of the internal paper feeding unit 16 or a paper feeding roller 17*a* of the manual paper feeding unit 17. The toner image on the recording paper is conveyed to the fixing unit 15. The toner image is sufficiently heated by the heating roller 15*a*, thereby fixed on the recording paper by fusion, and ejected to the outside.

The color laser printer 100 of the present embodiment employs a charger of a scorotron charger method for the charging unit 103*a*. As a result, an ozone gas component is generated at least at the periphery of four visible image forming units pa, pb, pc, and pd. In order to exhaust the ozone gas component, the color laser printer 100 is provided with the first exhaust duct (exhaust duct) 21 extending to an opening section on a lateral side of the housing 20.

In addition, the fixing unit 15 etc. generate volatile component gas, heat, and so on. In order to exhaust the volatile component gas and the heat, the second exhaust duct 22 extending to a top opening section of the housing 20 is provided at the periphery of the fixing unit 15.

Figure 3:
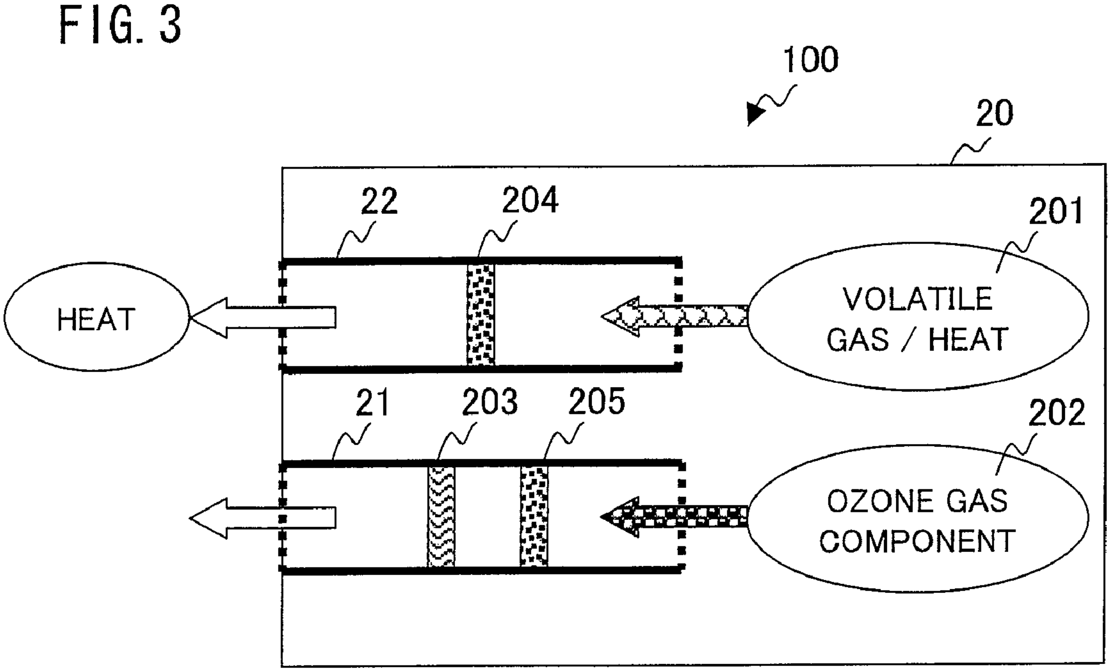
FIG. 3 is a schematic view illustrating structures of the exhaust ducts provided in the color laser printer in accordance with the embodiment of the present invention.

FIG. 3 is a schematic view illustrating structures of the exhaust ducts provided inside the housing 20 of the color laser printer 100. An exhaust fan not shown in FIG. 3 is provided inside the second exhaust duct 22. Besides, as illustrated in FIG. 3, the second exhaust duct 22 is therein provided with an activated carbon honeycomb filter 204 for VOC (Volatile Organic Compounds) gas treatment. Due to this arrangement, gas 201 containing volatile gas components and the heat generated by the fixing unit 15 etc. flows into the second exhaust duct 22. The volatile gas components in the gas 201 are decomposed and/or absorbed by the activated carbon honeycomb filter 204 for VOC gas treatment. After the removal of the volatile gas components, residual gas components, heat, etc. are exhausted to the outside of the housing 20.

The first exhaust duct 21, as well as the second exhaust duct 22, is therein provided with an exhaust fan. Besides, the first exhaust duct 21 is therein provided with a catalytic honeycomb filter 205 for ozone gas treatment (ozone treatment filter) and an ion emitting unit (ion emitting section) 203.

Figure 1:
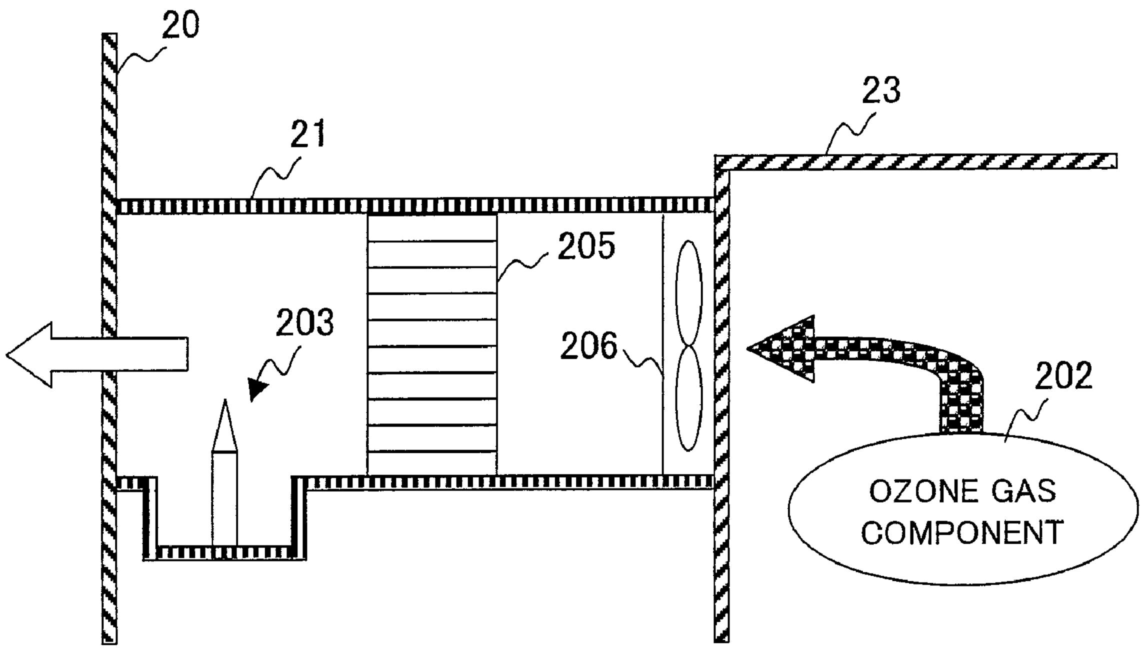
FIG. 1 is a cross-sectional view illustrating a structure of a first exhaust duct provided in a color laser printer in accordance with one embodiment of the present invention.

FIG. 1 is a cross-sectional view illustrating a detailed structure of the first exhaust duct 21. As illustrated in FIG. 1, both ends of the first exhaust duct 21 are supported by the housing 20 and a supporting member 23 provided therein. The first exhaust duct 21 is therein provided with, from the upstream side of exhaust (the side of the supporting member 23), an exhaust fan 206, the catalytic honeycomb filter 205 for ozone gas treatment, and the ion emitting unit 203 in this order.

The catalytic honeycomb filter 205 for ozone gas treatment may be anything which decomposes and/or absorbs ozone gas, for example, a high-purity activated carbon material or a non-noble metal catalyst, both of which are formed into a honeycomb geometry. Obviously, both the high-purity activated carbon material and the non-noble metal catalyst may be used for the catalytic honeycomb filter 205 for ozone gas treatment. An ozone decomposing filter commercially available from Shinko Actec Co., Ltd. http://www.shinko-actec-.co.jp/filter/ozone.html for example, may be used for such catalytic honeycomb filter 205 for ozone gas treatment. The ion emitting unit 203 is for emitting negative ions into an atmosphere.

The color laser printer 100 of the present embodiment is characterized in that the ion emitting unit 203 as well as the catalytic honeycomb filter 205 for ozone gas treatment is used for removal of ozone. Accordingly, in the present embodiment, an ozone removal device of the present invention includes at least the ion emitting unit 203. An ozone gas component 202 is caused by the exhaust fan 206 to flow into the first exhaust duct 21. Most of the ozone gas component 202 is removed by the catalytic honeycomb filter 205 for ozone gas treatment. Specifically, the ozone gas component is absorbed by the catalytic honeycomb filter 205 for ozone gas treatment or altered into a different substance due to a catalytic action by the catalytic honeycomb filter 205 for ozone gas treatment. The rest of the ozone gas component, which was not removed by the catalytic honeycomb filter 205 for ozone gas treatment, is altered into a different substance due to an action of the negative ions emitted by the ion emitting unit 203.

Figure 4:
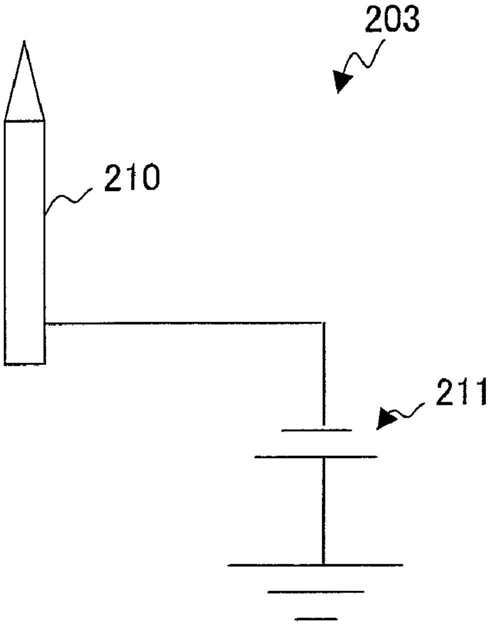
FIG. 4 is a schematic view illustrating one structure of an ion emitting unit in accordance with the embodiment of the present invention.

The ion emitting unit 203 is required to stably generate a constant amount of negative ions and little ozone at the generation of negative ions. As long as this is satisfied, an ion emitting unit of any form may be used for the ion emitting unit 203. FIG. 4 is a schematic view illustrating a structure of the ion emitting unit 203 of the present embodiment. In the present embodiment, as illustrated in FIG. 4, the ion emitting unit 203 includes a metallic needle-like member (needle electrode) 210 and an electric source 211. A negative electrode of the electric source 211 is connected to the needle-like member 210 whereas a positive electrode thereof is grounded. Therefore, a negative electric potential is applied on the metallic needle-like member 210.

The needle-like member 210 can be made by processing a rod-like metallic member in order that an end thereof is sharp. The needle-like member 210 serves as a needle electrode. Because the needle-like member 210 is required to be durable and electrically conductive, a material thereof may be iron, stainless steel, gold, silver, copper, tungsten, or the like. Among these materials, tungsten is preferable because the needle-like member 210 made of tungsten does not rust and does not easily change the shape of the needlepoint thereof due to a voltage.

The electric source 211 applies a voltage on the needle-like member 210 as a needle electrode. As a result, an electric field is concentrated on the needlepoint of the needle-like member 210 so that an air around the needlepoint is ionized. Positive ions are generated by applying a positive electric potential on the needle-like member 210; negative ions are generated by applying a negative electric potential on the needle-like member 210. In the present embodiment, negative ions are generated because a negative electric potential is applied on the needle-like member 210. Negative ions are generated from components of the air (mainly $N_2$ and $O_2$) around the needlepoint of the needle-like member 210. Because $N_2$ is energetically more stable than $O_2$, a main component of negative ions is considered to be $O_2^{-}$.

In the case where a voltage applied by the electric source 211 is too high, a large electric discharge occurs on the needlepoint. As a result, a large amount of ozone is generated at the same time as ion generation. In addition, the needlepoint of the needle-like member 210 becomes round and dull and corona products adhere thereto. This leads to a decrease in ion emission. Therefore, the voltage applied by the electric source 211 is preferably slightly below a level at which an electric discharge breaks out.

In the present embodiment, a needle-like member of tungsten whose needlepoint has curvature radius of approximately 50 μm is used for the needle-like member 210. The voltage applied by the electric source 211 is set to 10 kV. Accordingly, an electric potential of the needle-like member 210 is set to −10 kV and negative ions are thereby generated at the periphery of the needlepoint.

Figure 5:
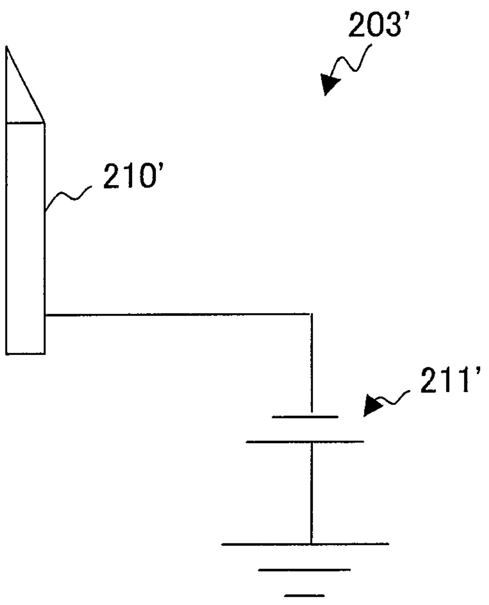
FIG. 5 is a schematic view illustrating another structure of the ion emitting unit in accordance with the embodiment of the present invention.

In the present embodiment, as illustrated in FIG. 4, a conic member is used for the needle-like member 210. However, the present invention is not limited to this. That is, as illustrated in FIG. 5, the needle-like member 210 may be a rod-like metallic member with an inclined cut edge. A needle-like member (needle electrode) 210' in such a shape makes the same effect as the needle-like member 210.

It is evident that the ion emitting unit 203 has indeed an effect of decreasing the ozone gas component in an atmosphere according to the experiment below. It is inferred that the effect is theoretically explained by the reason below.

Processes of ozone generation in the visible image forming unit include the steps represented by the expressions (1) to (3) below (Seidenki gakkaishi, 2001; 25(2): pp. 101-104).

$$O_2+e \rightarrow O_2^{+}+2e \quad (1)$$

$$O_2+e \rightarrow 2O+e \quad (2)$$

$$O_2+O+M \rightarrow O_3+M \quad (3)$$

("M" may be circumjacent catalyst metal or $O_2$). Firstly, an electron collides with an oxygen molecule in the air, so that the oxygen molecule is ionized (Expression (1)). Secondly, an electron generated here collides with another oxygen molecule, so that the oxygen molecule is dissociated (Expression (2)). Ozone is generated from a dissociated oxygen atom and an oxygen molecule (Expression (3)). Ozone is continuously generated by repeating the processes.

As for ozone decomposition, it is inferred that collision of an electron with an ozone molecule results in decomposition into an oxygen molecule and an oxygen atom as in Expression (4) presented below.

$$O_3+e \rightarrow O_2+O+e \quad (4)$$

An energy at ionization of an oxygen molecule: 1181 kJ/mol and an energy at dissociation of an oxygen molecule: 493.6 kJ/mol are relatively high whereas an energy at dissociation of an ozone molecule: 102 kJ/mol is low. Therefore, it is considered to be relatively easy that negative ions generated by the ion emitting unit 203 fulfill a role of the electron "e" in Expression (4). Accordingly, it is considered that ozone decomposition by negative ions generated by the ion emitting unit 203 is possible enough.

Although the present embodiment described an arrangement that the ion emitting unit 203 for decomposing ozone is provided in the color laser printer which is a color image forming apparatus, application of the ion emitting unit 203 is not limited to the color image forming apparatus. The ion emitting unit 203 is obviously applicable to a monochrome image forming apparatus such as a monochrome laser printer. Also, the ion emitting unit 203 is applicable to an image forming apparatus of a method other than the electrophotographic method, for example, an ion flow method.

In addition to the image forming apparatus, the ion emitting unit 203 is further applicable to an electrostatic air cleaning apparatus for dust, a waste ozone treatment device to treat waste ozone emitted from an oxidation apparatus based on oxidizability of ozone (the oxidation apparatus is used for, for example, oxidative decomposition of harmful substance generated at industrial plants etc., and a manufacturing process of an $SiO_2$ film that is an insulating film required for a thin film transistor, and the like), and a preservation apparatus for fruits and vegetables utilizing an antiseptic effect of ozone (for example, a refrigerator).

Thus, for ozone removal, the ion emitting unit 203 of the present embodiment is applicable to a wide variety of apparatuses.

Embodiment 2

Another embodiment of the present invention is described below with reference to FIGS. 8 and 9. For convenience of explanation, members with the same functions as those of members of Embodiment 1 are given the same reference numerals and explanations thereof are omitted. In the present embodiment, too, an explanation will be made as to a case where the ozone removal device of the present invention is applied to a color laser printer which is an image forming apparatus.

Figure 8:
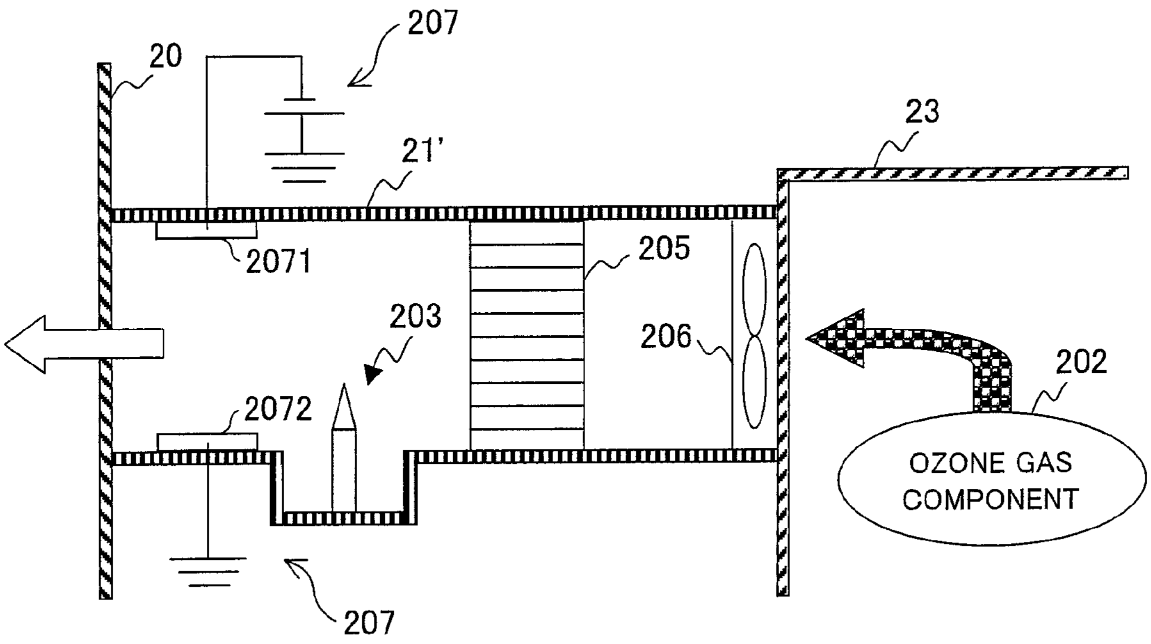
FIG. 8 is a cross-sectional view illustrating a structure of a first exhaust duct provided in a color laser printer in accordance with another embodiment of the present invention.
Figure 9:
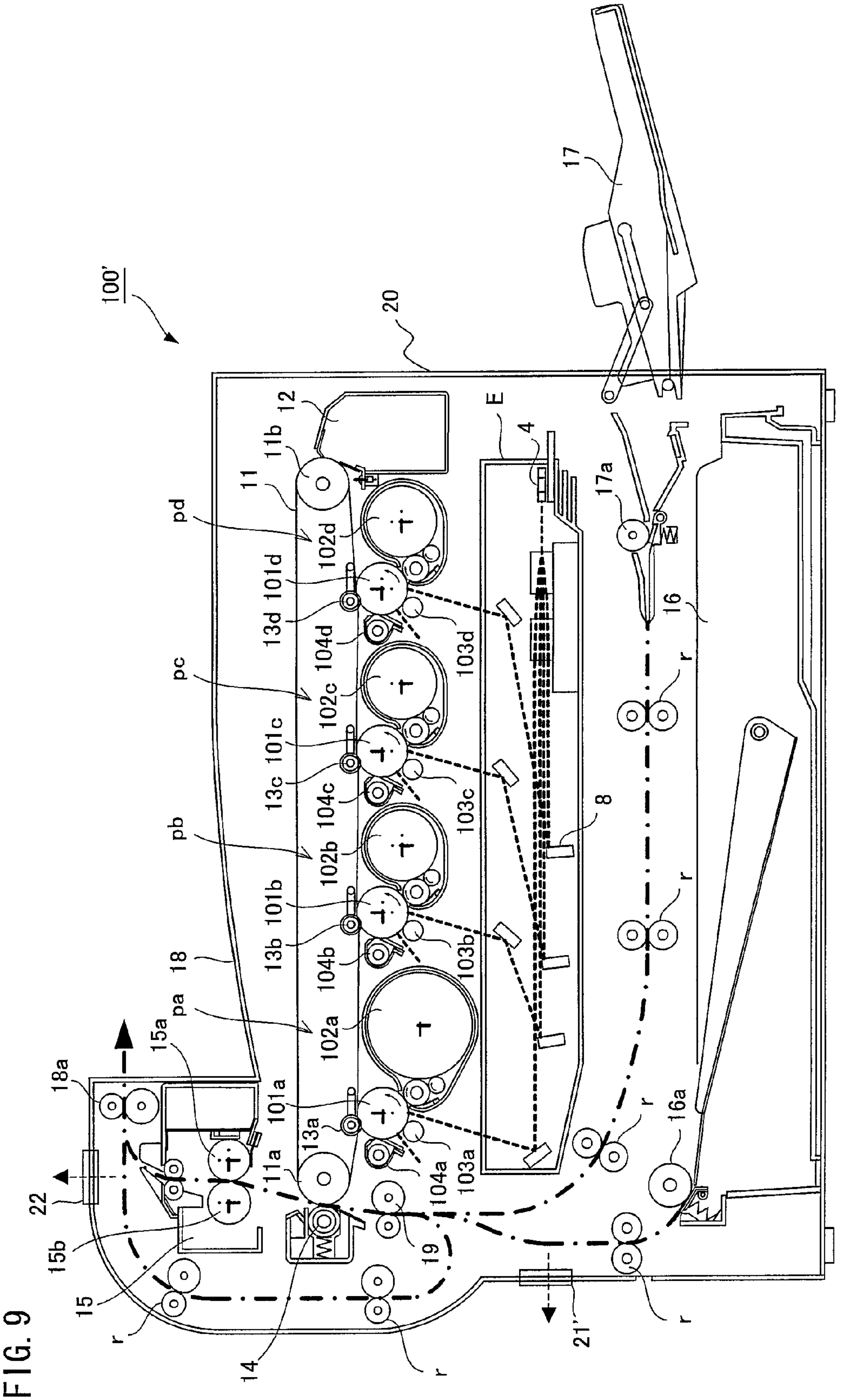
FIG. 9 is a cross-sectional view illustrating a schematic structure of the color laser printer in accordance with another embodiment of the present invention.

As illustrated in FIG. 9, a color laser printer 100' of the present embodiment is basically the same as the color laser printer of Embodiment 1 except that the color laser printer 100' includes a first exhaust duct 21' instead of the first exhaust duct 21. What is different between the first exhaust duct 21' and the first exhaust duct 21 is that, inside the first exhaust duct 21', as illustrated in FIG. 8, an electric field forming unit (electric field forming section) 207 is provided in order to generate an electric field downstream of the ion emitting unit 203. Except for this structure, the color laser printer 100' of the present embodiment is the same as the color laser printer 100 of Embodiment 1.

FIG. 8 is a cross-sectional view illustrating a detailed structure of the first exhaust duct 21'. As illustrated in FIG. 8, both ends of the first exhaust duct 21' are supported by the housing 20 and a supporting member 23 provided therein. From the upstream side of exhaust (the side of the supporting member 23), the first exhaust duct 21' is therein provided with the exhaust fan 206, the catalytic honeycomb filter 205 for ozone gas treatment, the ion emitting unit 203, and the electric field forming unit 207 in this order. The color laser printer of the present embodiment is characterized in that the electric field forming unit 207 is provided downstream of the ion emitting unit 203. That is, in the present embodiment, an ozone removal device of the present invention includes at least the ion emitting unit 203 and the electric field forming unit 207.

The electric field forming unit 207 is required to form a stable and uniform electric field. As long as this is satisfied, an electric field forming unit of any form may be used for the electric field forming unit 207. In the present embodiment, the electric field forming unit 207 is provided downstream of the ion emitting unit 203 so as to generate an electric field perpendicularly to a direction of an ozone stream.

In the present embodiment, the electric field forming unit 207 includes conductive members with a certain space therebetween. An electric field is generated by making a potential difference between the conductive members. Specifically, the conductive members are conductive flat plates 2071 and 2072, which are located on inner walls facing each other of the first exhaust duct 21 with a certain space between the conductive flat plates 2071 and 2072. A material for the conductive flat plates 2071 and 2072 is required to be conductive and capable of retaining the shape thereof for a long period. For example, the conductive flat plates 2071 and 2072 can be mainly made of metals such as stainless steel, iron, gold, silver, and copper. Although organic conductive materials can be also used, heat due to energization is generated in the case of a relatively high electric resistance. Due to the heat, the conductive flat plates 2071 and 2072 change shapes thereof and thereby cannot keep the certain distance therebetween. Because this may make it difficult to form a uniform electric field, it is preferable to select a material whose electric resistance is the lowest possible. In the present embodiment, the conductive flat plates 2071 and 2072 are made of stainless steel, which does not rust and easily change the shape thereof. In order to form an electric field, a negative electric potential is allocated to the conductive flat plate 2071 whereas the conductive flat plate 2072 is grounded.

There is an ozone reduction effect as described in Embodiment 1 by the emission of negative ions. In the present embodiment, there is a further ozone reduction effect by additionally forming an electric field in the vicinity of the ion emitting unit 203. From the experiments below, it is evident that the ion emitting unit 203 and the electric field forming unit 207 indeed reduce (decompose) the ozone gas component in an atmosphere by forming an electric field and emitting negative ions.

EXAMPLE 1

An ozone decomposition effect by the ion emitting unit 203 was verified through the experiment below with the color laser printer 100 of Embodiment 1.

Experiment 1

In order to assess performance of the ion emitting unit 203, an amount of emitted negative ions was measured with an ionometer AIC-2000 of Sato Shouji, Inc. As a result, it was ascertained that even at a location 60 cm away from the needlepoint, twenty million ions/cc were stably emitted. Also, it was ascertained that an ozone concentration was 0.001 ppm or less through a measurement of an amount of ozone generation with an EG-2001F (of an ultraviolet absorption method) of Ebara Jitsugyo Co., Ltd.

From these results, it was confirmed that the ion emitting unit 203 of Embodiments 1 and 2 could stably generate certain amount of negative ions and, at the same time, little ozone was generated.

Experiment 2

The catalytic honeycomb filter 205 for ozone gas treatment was removed from the color laser printer 100 so as to provide the color laser printer 100' for removing the ozone gas component only with the ion emitting unit 203. This color laser printer 100' was located inside a closed chamber whose volume is approximately 9 $m^3$. Thus, transition of an ozone concentration in the chamber was measured for a case of continuous two-side printing for 15 minutes. The EG-2001F (of an ultraviolet absorption method) of Ebara Jitsugyo Co., Ltd. was used for the measurement of the ozone concentration.

An electric voltage was applied on the ion emitting unit 203 during an operation of the exhaust fan 206 (not only during printing, but also during a warming-up time before printing and a cooling-down time after printing) in order for the ion emitting unit 203 to emit negative ions.

As a comparative example, measurement was also carried out for a case where the ion emitting unit 203 did not operate and accordingly negative ions were not emitted. In the present experiment, each measurement above was carried out two times.

Figure 6:
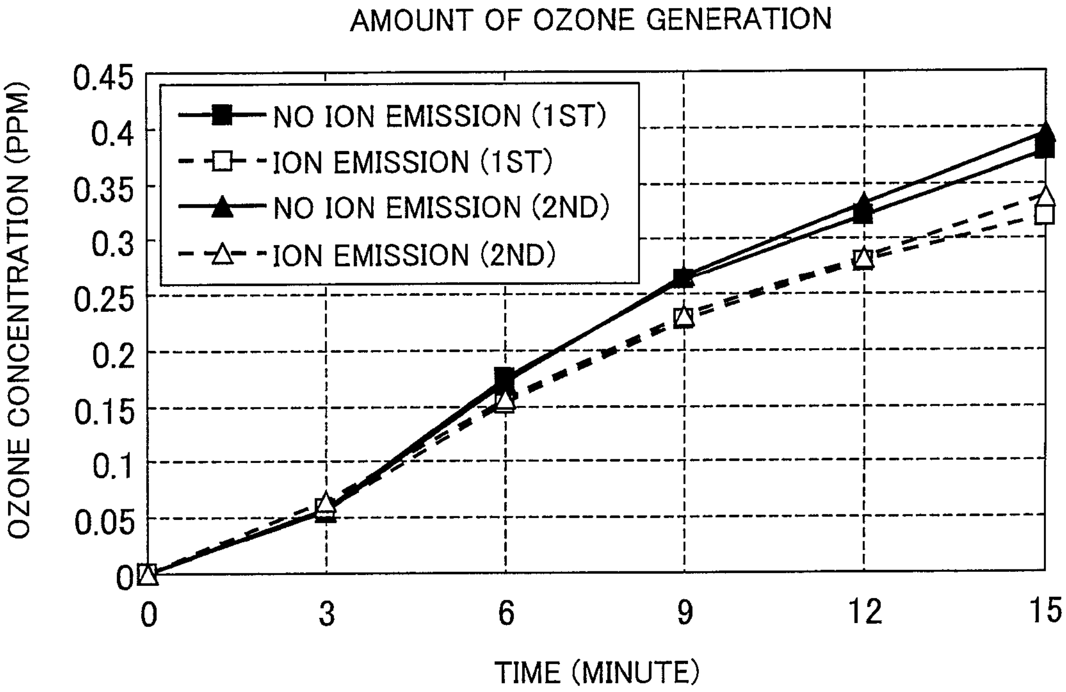
FIG. 6 is a graph showing an ozone removal effect by the ion emitting unit.

FIG. 6 shows the result of the present experiment. In the graph of FIG. 6, the continuous lines represent results of cases where negative ions were not generated; the dashed lines represent results of cases where negative ions were generated. As shown in FIG. 6, for both the first and the second times, cases where the ion emitting unit 203 operated showed a lower ozone concentration in the chamber at each time point than cases where the ion emitting unit 203 did not operate. From these results, it was demonstrated that the negative ions emitted by the ion emitting unit 203 had an effect of reducing an ozone concentration.

Experiment 3

With the color laser printer 100 having both the catalytic honeycomb filter 205 for ozone gas treatment and the ion emitting unit 203, transition of an ozone concentration in the chamber was measured under the same conditions as Experiment 1 with the ion emitting unit 203 working.

As a comparative example, measurement was also carried out for a case where the ion emitting unit 203 did not operate and accordingly negative ions were not emitted.

Figure 7:
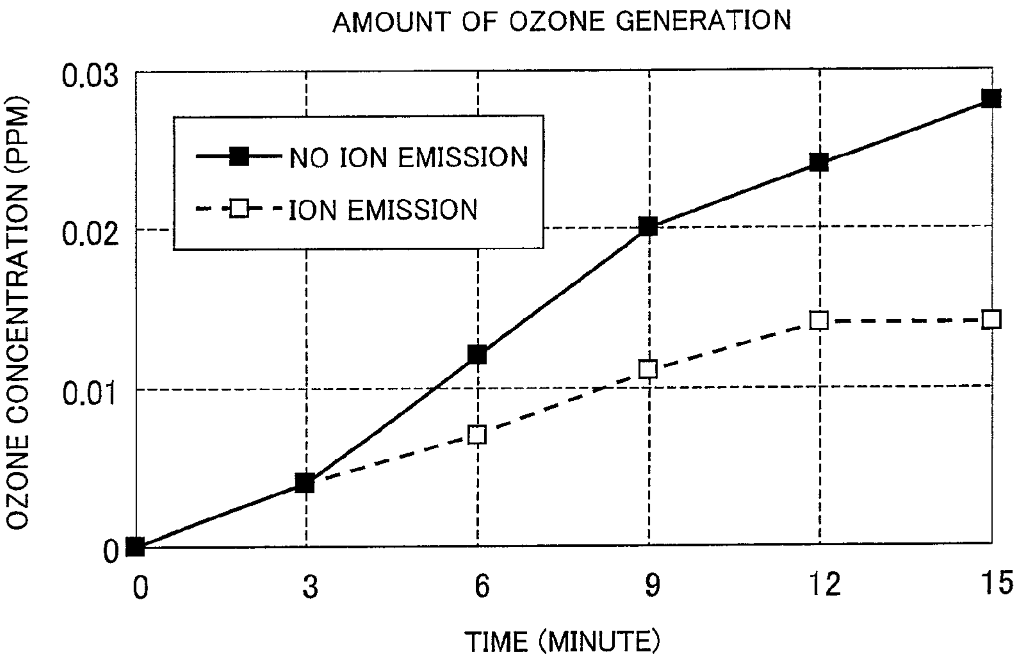
FIG. 7 is a graph showing an ozone removal effect by combination of the ion emitting unit and a catalytic honeycomb filter for ozone gas treatment.

FIG. 7 is a graph showing the result of the present experiment. In the graph of FIG. 7, the continuous line represents a result of a case where negative ions were not generated; the dashed line represents a result of a case where negative ions were generated. As shown in FIG. 7, in the case where the ion emitting unit 203 operated, an ozone concentration in the chamber at each time point lowered at about half a level of a case where the ion emitting unit 203 did not operate. From these results, as well as Experiment 2, it was demonstrated that the negative ions emitted by the ion emitting unit 203 had an effect of reducing an ozone concentration.

In addition, in the case where the catalytic honeycomb filter 205 for ozone gas treatment was not used, an ozone concentration at the time point of 15 minutes exceeded 0.3 ppm as shown in the result of Experiment 2 (FIG. 6). In contrast, in the case where the catalytic honeycomb filter 205 for ozone gas treatment was used, the ozone concentration at the time point of 15 minutes was successfully suppressed at a level of approximately 0.015 ppm. This shows that the combination of the catalytic honeycomb filter 205 for ozone gas treatment and the ion emitting unit 203 was especially effective for ozone removal.

Since the catalytic honeycomb filter 205 for ozone gas treatment was not used in Experiment 2, the ion emitting unit 203 was surrounded by the atmosphere containing a high concentration of ozone. In the present experiment, on the other hand, the ion emitting unit 203 was surrounded by the atmosphere containing a relatively low concentration of ozone because the catalytic honeycomb filter 205 for ozone gas treatment was used. Comparison between the result of Experiment 2 (FIG. 6) and the result of the present experiment (FIG. 7) shows that the arrangement of the present experiment in which the ion emitting unit 203 was located in the atmosphere containing a relatively low concentration of ozone realized a higher ozone removal efficiency than the arrangement of Experiment 2. Therefore, an ozone concentration in an environment in which the ion emitting unit 203 is located is preferably not very high. Specifically, a preferable ozone concentration is approximately 0.1 ppm or less.

EXAMPLE 2

An ozone decomposition effect by the ion emitting unit 203 and the electric field forming unit 207 was verified through the experiments below with the color laser printer 100' of Embodiment 2.

Experiment 5

The color laser printer 100' having the catalytic honeycomb filter 205 for ozone gas treatment, the ion emitting unit 203, and the electric field forming unit 207 was located inside a closed chamber whose volume was approximately 9 $m^3$. Thus, transition of an ozone concentration in the chamber was measured for a case of continuous two-side printing for 15 minutes. The EG-2001F (of an ultraviolet absorption method) of Ebara Jitsugyo Co., Ltd. was used for the measurement of the ozone concentration.

The electric voltage of −10 kV was applied on the ion emitting unit 203 during the operation of the exhaust fan 206 (not only during printing, but also during a warming-up time before printing and a cooling-down time after printing) in order for the ion emitting unit 203 to emit negative ions. In addition, the electric field forming unit 207 formed an electric field (0.6 MV/m) in synchronization with the operation of the ion emitting unit 203.

Figure 10:
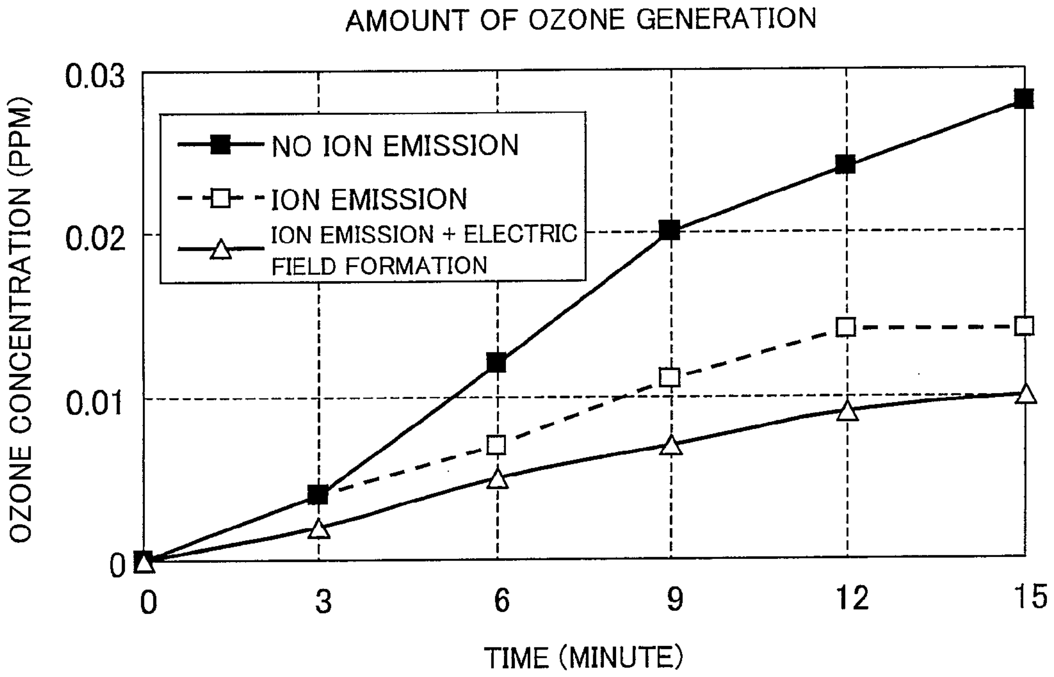
FIG. 10 is a graph showing an ozone removal effect by the ion emitting unit and an electric field forming unit.

FIG. 10 is a graph showing the result of the present experiment. For the sake of a comparison with the result of the present experiment (ion emission+electric field formation), the graph of FIG. 10 shows the result of Experiment 3 (ion emission) and the result of the comparative example of Experiment 3 (no ion emission).

As shown in FIG. 10, an amount of ozone generation in the case of an ion emission without electric field formation is about a half of an amount of ozone generation in the case of no ion emission. In addition, an amount of ozone generation in the case of electric field (0.6 MV/m) formation and an ion emission is approximately 20% smaller than an amount of ozone generation in the case of an ion emission without electric field formation.

In a case where the electric field forming unit 207 was provided upstream of the ion emitting unit 203, an ozone reduction effect was the same as the case where only the ion emitting unit 203 was provided, that is, Experiment 3. The reason for this result is considered as follows: Providing the electric field forming unit 207 downstream of the ion emitting unit 203 as in the present example allows negative ions to react with ozone in an electric field region, which facilitates dissociation of oxygen molecules. On the other hand, in a case where the electric field forming unit 207 is provided upstream of the ion emitting unit 203, it is considered that the reaction cannot be activated because there are few negative ions in an electric field region.

Experiment 6

Figure 11:
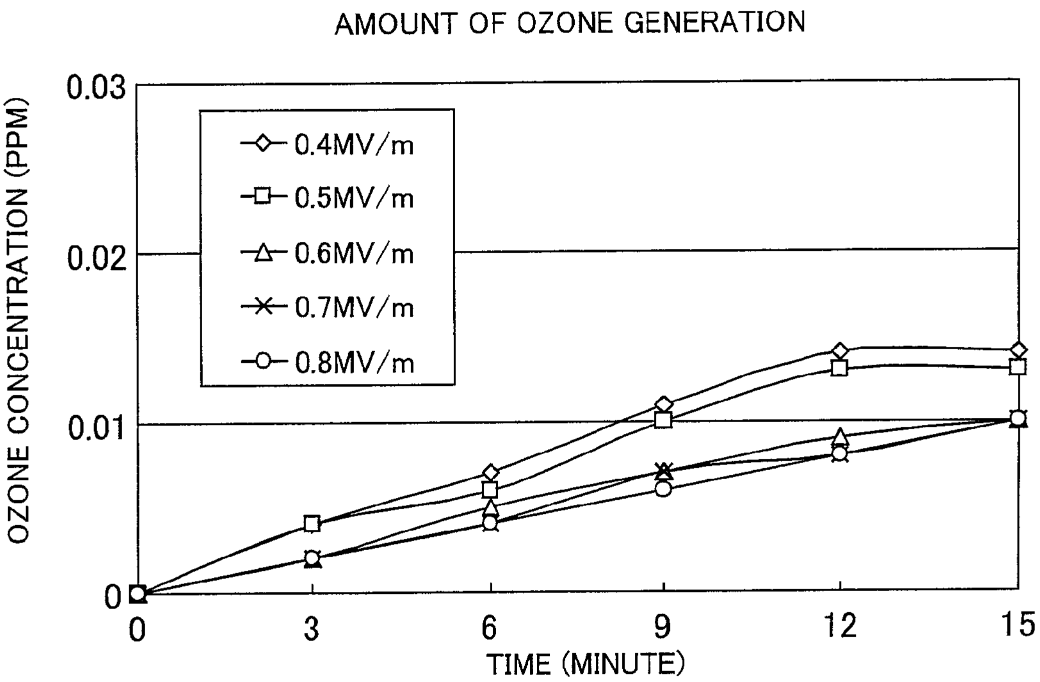
FIG. 11 is a graph showing an ozone removal effect by the ion emitting unit and the electric field forming unit in a case where the electric field forming unit forms electric fields with different levels.

Under the same conditions as Experiment 5, an ozone concentration was measured changing only intensity of an electric field formed by the electric field forming unit 207. FIG. 11 shows the result of Experiment 6. As shown in FIG. 11, as the intensity of the formed electric field was higher, an amount of ozone generation decreased. In addition, it was observed that forming an electric field higher than a threshold: 0.6 MV/m made no further effect.

From the results of Experiments 5 and 6, it was found that an amount of ozone could be effectively reduced (decomposed) by forming an electric field and the emission of negative ions. In addition, it was found that an amount of ozone reduction becomes larger by forming a higher electric field, but an ozone reduction effect at a higher intensity of an electric field than 0.6 MV/m is almost the same as that at the intensity of 0.6 MV/m.

As described above, the ozone removal device of the present invention includes an ion emitting section for emitting negative ions into an atmosphere containing ozone.

The ion emitting section may include a needle electrode and an electric source for applying a negative electric potential on the needle electrode.

According to the arrangement, the electric source applies a negative electric potential on the needle electrode. As a result, negative ions are generated and emitted into the atmosphere in the vicinity of the needle electrode. An amount of generation of negative ions depends on a level of voltage (a level of an electric potential of the needle electrode) applied by the electric source. Therefore, setting a voltage of the electric source to an appropriate value allows stable generation of negative ions with an amount enough to remove ozone.

The ozone removal device of the present invention may further include an electric field forming section for forming an electric field in an area through which the ozone passes in a vicinity of the ion emitting section.

According to the arrangement, in the vicinity of the ion emitting section, the electric field forming section forms an electric field in an area through which the ozone passes. As a result, a further ozone reduction effect can be obtained.

In addition to the arrangement, the ozone removal device of the present invention is preferably arranged such that the electric field forming section and the ion emitting section are provided on a flow path of an airflow flowing in one direction in such a manner that the electric field forming section is provided on a downstream side of the airflow in relation to the ion emitting section. This is because a further ozone reduction effect can be obtained by locating the electric field forming section on the downstream side of the airflow in relation to the ion emitting section. Specifically, by locating the electric field forming section on the downstream side of the airflow in relation to the ion emitting section, dissociation of oxygen molecules is facilitated through reaction of negative ions with ozone in an electric field region. As a result, ozone can be effectively reduced. In contrast, providing the electric field forming section on the upstream side of the airflow in relation to the ion emitting section results in generation of few negative ions. As a result, ozone cannot be reduced.

In order to attain the object above, the image forming apparatus of the present invention includes: an image forming section for forming an image on a recording medium by a method involving ozone generation; a housing for covering the image forming section; and an ozone removal device having an ion emitting section for emitting negative ions into an atmosphere containing ozone, the ozone removal device being provided inside the housing.

Some image forming apparatuses, for example, an electrophotographic image forming apparatus having a corona charger and the like form an image by a method involving ozone generation. A large amount of ozone generated therein can cause a problem in image formation. For example, due to generation of a high concentration of ozone inside the electrophotographic image forming apparatus, products of ozone (such as NOx) adhere to the surface of the photoreceptor. This can cause a charge diffusion of the photoreceptor and result in an image defect, what is called an image blurring.

However, according to the arrangement of the present invention, it is possible to remove ozone generated by the image forming section because the ozone removal device is provided inside the housing of the image forming apparatus. Accordingly, this makes it possible to prevent various adverse effects brought by ozone generation.

The image forming apparatus further includes: an exhaust duct for exhausting gas inside the housing to an outside and the ozone removal device being preferably provided inside the exhaust duct.

According to the arrangement, an ozone concentration inside the housing can be reduced because the exhaust duct exhausts ozone in the housing to the outside. Also, the ozone removal device is provided inside the exhaust duct, so that it is possible to reduce an ozone concentration of exhaust to be exhausted to the outside of the housing via the exhaust duct. This makes it possible to prevent generation of stench around the image forming apparatus. Besides, in a small room, for example, a discharged exhaust may return into the housing of the image forming apparatus. Even in such a case, it is possible to prevent an ozone concentration in the housing from increasing through ozone removal by the ion emitting section at exhaust.

The image forming apparatus preferably further includes an ozone treatment filter for decomposing and/or absorbing ozone, the ozone treatment filter being provided inside the exhaust duct.

According to the arrangement, an amount of ozone removal is significantly improved because the ozone treatment filter is provided in addition to the ozone removal device. Besides, the ion emitting unit also removes ozone, in contrast to a conventional arrangement in which the ozone treatment filter solely removes ozone. As a result, a life of the ozone treatment filter becomes longer. This makes it possible to reduce the number of replacements of the filter.

Inside the exhaust duct, the ozone treatment filter is preferably provided on an upstream side of exhaust in relation to the ozone removal device.

According to the arrangement, an ozone removal effect can be significantly improved because residual ozone is removed by the ozone removal device after decomposition and/or absorption of most of ozone by the ozone treatment filter.

The ozone removal device is preferably provided in an atmosphere whose ozone concentration is 0.1 ppm or less.

As the experiments above show, an ozone removal efficiency is higher in a case where the ozone removal device is located in the atmosphere whose ozone concentration is not very high. Therefore, the arrangement makes it possible to effectively remove ozone.

In order to attain the object above, an ozone removal method of the present invention is for removing ozone in a gas, including the step of emitting negative ions into the gas.

As a result of a keen examination on a method for removing ozone, the inventors of the present invention found that the negative ions emitted into an atmosphere have an ozone reduction effect although the mechanism of this action is unclear. According to the method, because negative ions are emitted into a gas by the step of emitting ions, an ozone concentration in the gas is reduced by the emitted negative ions. Accordingly, ozone removal can be carried out.

The ozone removal method may further include the step of forming an electric field in an area into which the negative ions are emitted and through which the ozone passes.

The ozone removal method preferably further includes the step of, before the step of emitting negative ions into the gas, making the gas pass through an ozone treatment filter for decomposing and/or absorbing ozone.

According to the arrangement, an ozone removal effect can be significantly improved because residual ozone is removed by negative ions after decomposition and/or absorption of most of ozone by the step of filter treatment.

Since ozone in an atmosphere can be removed according to the present invention, the present invention is applicable to various apparatuses which require ozone removal. For example, the present invention is applicable to an image forming apparatus, a static air cleaning apparatus for dust, a waste ozone treatment device for an oxidation apparatus based on oxidizability of ozone, a preservation apparatus for fruits and vegetables utilizing an antiseptic effect of ozone, etc.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

What is claimed is:

1. An ozone removal device, comprising:
an ion emitting section including:
a needle electrode; and
an electric source for applying a negative electric potential on the needle electrode,
said ion emitting section causing the electric source to apply a negative voltage to the needle electrode so as to generate negative ions on a needlepoint of the needle electrode,
the voltage applied to the needle electrode being at a level where no electric discharge breaks out,
said ion emitting section being provided in an atmosphere containing ozone,
said ion emitting section emitting the negative ions so as to remove the ozone.

2. The ozone removal device according to claim 1, wherein the needle electrode is made of at least one of iron, stainless steel, gold, silver, copper, and tungsten.

3. The ozone removal device according to claim 1, further comprising an electric field forming section for forming an electric field in an area through which the ozone passes in a vicinity of the ion emitting section.

4. The ozone removal device according to claim 3, wherein the electric field forming section and the ion emitting section are provided on a flow path of an airflow flowing in one direction in such a manner that the electric field forming section is provided on a downstream side of the airflow in relation to the ion emitting section.

5. The ozone removal device according to claim 3, wherein the electric field forming section comprises conductive members facing each other and forms an electric field by making a potential difference between the conductive members.

6. An image forming apparatus, comprising:
an image forming section for forming an image on a recording medium by a method involving ozone generation;
a housing for covering the image forming section; and
an ozone removal device provided inside the housing, said ozone removal device including:
a needle electrode; and
an electric source for applying a negative electric potential on the needle electrode,
said ion emitting section causing the electric source to apply a negative voltage to the needle electrode so as to generate negative ions on a needlepoint of the needle electrode,
the voltage applied to the needle electrode being at a level where no electric discharge breaks out,
said ion emitting section being provided in an atmosphere containing ozone,
said ion emitting section emitting the negative ions so as to remove the ozone.

7. The image forming apparatus according to claim 6, further comprising
an exhaust duct for exhausting gas inside the housing to an outside,
the ozone removal device being provided inside the exhaust duct.

8. The image forming apparatus according to claim 7, further comprising another exhaust duct, the exhaust duct exhausting at least one of a volatile component gas and heat out of the housing.

9. The image forming apparatus according to claim 7, further comprising an ozone treatment filter for decomposing and/or absorbing ozone, the ozone treatment filter being provided inside the exhaust duct.

10. The image forming apparatus according to claim 9, wherein, inside the exhaust duct, the ozone treatment filter is provided on an upstream side of exhaust in relation to the ozone removal device.

11. The image forming apparatus according to claim 9, wherein the ozone treatment filter contains at least one of a high-purity activated carbon material and a non-noble metal catalyst.

12. The image forming apparatus according to claim 9, wherein an exhaust fan is provided on an upstream side of exhaust in relation to the ozone treatment filter.

13. The image forming apparatus according to claim 6, wherein the ozone removal device is provided in an atmosphere whose ozone concentration is 0.1 ppm or less.

14. An ozone removal method for removing ozone in a gas, comprising the steps of:
emitting negative ions into the gas from an ion emitting section having a needle electrode and an electric source for applying a negative electric potential on the needle electrode; and
removing ozone with use of the negative ions emitted by the ion emitting section,
a voltage applied by the electric source in the step of emitting negative ions, the voltage being at a level where, on a needlepoint of the needle electrode, negative ions are generated and no electric discharge breaks out.

15. The ozone removal method according to claim 14, further comprising the step of forming an electric field in an area into which the negative ions are emitted and through which the ozone passes.

16. The ozone removal method according to claim 14, further comprising the step of, before the step of emitting negative ions into the gas, making the gas pass through an ozone treatment filter for decomposing and/or absorbing ozone.

* * * * *